United States Patent
Al Farra et al.

(10) Patent No.: US 12,339,207 B2
(45) Date of Patent: Jun. 24, 2025

(54) DEVICE AND METHOD FOR DETECTING THE FLOCCULATION THRESHOLD OF A COLLOIDAL MEDIUM, IN PARTICULAR A MEDIUM COMPRISING ASPHALTENES, BY ADDITION OF ALIPHATIC SOLVENT

(71) Applicant: TotalEnergies OneTech, Courbevoie (FR)

(72) Inventors: Ahmad Al Farra, Le Havre (FR); Jérôme Olivier, Le Havre (FR); Martial Lepinay, Mouen (FR); Jean Christien, Saint Martin de Fontenay (FR)

(73) Assignee: TotalEnergies One Tech, Courbevoie (FR)

( * ) Notice: Subject to any disclaimer, the term of this patent is extended or adjusted under 35 U.S.C. 154(b) by 374 days.

(21) Appl. No.: 18/012,492

(22) PCT Filed: Jun. 21, 2021

(86) PCT No.: PCT/EP2021/066878
§ 371 (c)(1),
(2) Date: Dec. 22, 2022

(87) PCT Pub. No.: WO2021/259876
PCT Pub. Date: Dec. 30, 2021

(65) Prior Publication Data
US 2023/0251177 A1 Aug. 10, 2023

(30) Foreign Application Priority Data
Jun. 23, 2020 (EP) .................................. 20305688

(51) Int. Cl.
*G01N 15/00* (2024.01)

(52) U.S. Cl.
CPC ..... *G01N 15/00* (2013.01); *G01N 2015/0092* (2013.01)

(58) Field of Classification Search
CPC ........ G01N 15/00; G01N 15/02; G01N 15/06; G01N 2015/0092; G01N 2015/139;
(Continued)

(56) References Cited

U.S. PATENT DOCUMENTS 3,761,187 A * 9/1973 Dittrich ................. G06M 1/101
250/576
5,883,378 A * 3/1999 Irish ........................ H01S 5/042
250/573

(Continued)

FOREIGN PATENT DOCUMENTS

| CN | 101805050 A | * | 8/2010 |
| FR | 2566909 A1 | | 1/1986 |
| WO | 2005/003754 A2 | | 1/2005 |

OTHER PUBLICATIONS

Andersen S I. "Flocculation onset titration of petroleum asphaltenes" Energy & Fuels, American Chemical Society, Washington, DC, US, vol. 13, No. 2, Feb. 20, 1999 (Feb. 20, 1999), pp. 315-322.

(Continued)

*Primary Examiner* — Abdullahi Nur
(74) *Attorney, Agent, or Firm* — Sughrue Mion, PLLC

(57) ABSTRACT

A device for measuring the flocculation threshold of a colloidal medium by varying the intensity of the luminous flux, and a method for measuring the flocculation threshold of a colloidal medium by the addition of aliphatic solvent using the device, including the step of determining the flocculation after the addition of the amount of aliphatic solvent necessary for flocculation.

15 Claims, 5 Drawing Sheets

(58) Field of Classification Search
CPC ...... G01N 21/028; G01N 21/83; G01N 21/51; G01J 3/42
See application file for complete search history.

(56) References Cited

U.S. PATENT DOCUMENTS

| | | | |
|---|---|---|---|
| 10,422,782 B2 | 9/2019 | Lloyd et al. | |
| 2009/0153855 A1* | 6/2009 | Bungo | G01J 3/0237 356/319 |
| 2016/0377530 A1 | 12/2016 | Barrett | |
| 2020/0150017 A1* | 5/2020 | Bates | G01N 15/0612 |

OTHER PUBLICATIONS

Written Opinion of PCT/EP2021/066878 dated Sep. 6, 2021.[PCT/ISA/237].
International Search Report of PCT/EP2021/066878 dated Sep. 6, 2021. [PCT/ISA/210].

* cited by examiner

DEVICE AND METHOD FOR DETECTING THE FLOCCULATION THRESHOLD OF A COLLOIDAL MEDIUM, IN PARTICULAR A MEDIUM COMPRISING ASPHALTENES, BY ADDITION OF ALIPHATIC SOLVENT

CROSS REFERENCE TO RELATED APPLICATIONS

This application is a National Stage of International Application No. PCT/EP2021/066878 filed Jun. 21, 2021, claiming priority based on European Patent Application No. 20305688.2 filed Jun. 23, 2020, the entire disclosures of which are incorporated herein by reference.

TECHNICAL FIELD

The subject of the invention is a new method for detecting the flocculation of asphaltenes, as well as an associated detection device for measuring light in heavy hydrocarbon products, waste oils, dirty water or any product containing an emulsion and, in particular, for measuring the flocculation threshold of a colloidal medium.

PRIOR ART

Petroleum products, and in particular fuel oils or petroleum distillation residues, generally referred to as "black products" in the industry, are colloidal systems consisting of asphaltenes—namely heavy, highly aromatic molecules with paraffinic side-chains—which are dispersed (or also called "peptised") in the form of micelles in an oily phase. These colloidal systems can be destabilised more or less easily, for example by thermal cracking or by dilution. Thus, in a refinery, the conversion process, known as visbreaking, can lead to the precipitation of asphaltenes under the effect of high process temperatures (generally above 400° C.). Similarly, the constitution of mixtures containing such colloidal systems can generate precipitation of these asphaltenes by flocculation, particularly if the dilution environment is of the paraffinic type.

It is therefore necessary to know or estimate the characteristics of these asphaltenes in black products, such as a petroleum product or a mixture of hydrocarbon products, in order to assess their intrinsic stability, as well as their associated stability reserve. Indeed, the higher the stability reserve, the less the black product will be subject to problems of asphaltene precipitation, or compatibility by dilution with other chemical species, in particular paraffinic bases.

It should be noted that fuel oils or petroleum residues consist of a maltenic matrix (resins+paraffins) and asphaltenes dispersed in colloidal form. Asphaltenes which have very aromatic characteristics are insoluble with paraffins which have aliphatic characteristics. For a residue to be stable, it is necessary for the asphaltenes to be kept in suspension (or dispersed or peptised) in the oil matrix. The peptisation of asphaltenes is ensured by resins which have both aromatic characteristics and aliphatic characteristics. When a residue has been destabilised, the asphaltenes flocculate by agglomerating in the form of large particles which can cause clogging of filters in the various treatment units, or even to the deterioration of the metallurgy, for example fouling the pipes which leads to a loss of energy efficiency and pipe capacity.

The characteristic known as S-value, or even intrinsic stability, for example of a black product, is defined in the industry and in the ASTM D7157-18 standard (Revision 2018) by the following expression:

S=aromaticity of maltenes/aromaticity of asphaltenes, i.e. $S=S_o/(1-S_a)$, wherein, $S_o$ represents the ability of the medium to solubilise the asphaltenes, namely the aromatic characteristics of the medium. The more aromatic it is, the greater the So will be.

Sa is the aromatic characteristics of asphaltenes.

1−Sa represents the aromaticity of the medium necessary to solubilise the asphaltenes present.

If S>1, the asphaltenes are peptised and are therefore stable. S−1 represents the stability reserve (the higher the reserve, the less the black product will be subject to precipitation or compatibility problems).

The severity of a thermal shock, such as that brought about by distillation or visbreaking directly effects the aromaticity of the asphaltenes since the thermal cracking causes the alkyl chains to be cut and the asphaltenes to condense. The more condensed and less branched asphaltenes (weaker Sa) will need a stronger solvent to remain dispersed. Thus, the knowledge of the value of S, linked to that of Sa, will make it possible to specify the settings of the operating conditions of the unit concerned so that it can be operated without the risk of asphaltene precipitation, and consequently, to meet the various quality requirements of the operator.

Furthermore, knowledge of the solvent power values So and the aromatic characteristics of the asphaltenes Sa is necessary to optimise the combination of the various components of the fuel oils. Thus, if a fluxing agent (product capable of lowering the viscosity of a mixture) of low solvent power is added to a black product, for example visbroken, and having high So and low Sa values, the value of the So mixture is reduced, which can lead to a destabilisation of the black product, and consequently to flocculation of the asphaltenes, because the resulting So and Sa values would be too low to satisfy the S>1 relationship, i.e. the condition for said asphaltenes to be peptised, and therefore stable.

Usually, we determine the values of S and Sa in the laboratory, and then by calculation So, of a black product by a step dilution using a paraffinic solvent of said black product, previously mixed with an aromatic solvent. The moment when flocculation occurs is noted. The measurement is repeated for at least one other mixture with a different dilution rate. In this way, results are obtained which make it possible, by linear correlation, to obtain the desired values of S and Sa, then to deduce So by calculation.

Experimentally, the flocculation threshold in a given mixture can be detected using various optical probes operating in the infrared (IR) or near infrared (NIR).

For example, the technique described in patents FR-A-2 596 522 or U.S. Pat. No. 4,628,204, from Texaco Belgium SA company, makes it possible to measure by IR the flocculation threshold of a colloidal solution during its dilution. This measurement requires the correct choice of the optical measurement probe (there are various probes) depending on the nature and in particular the presence of asphaltenes to a greater or lesser extent in the black product to be tested. If the operator makes the wrong choice, it is then necessary to clean the equipment, then prepare the sample again for a new measurement with another probe, which results in a loss of time that can exceed one hour of operator time, whereas the time of an analysis is approximately 1.5 to 2 hours, especially if it is the choice of a different probe that proves to be judicious.

Another example is the method developed by Shell company, in collaboration with its Dutch partner Zematra, a manufacturer of analysis equipment. This method, wherein the detection of the flocculation threshold of the colloidal medium is carried out using a single probe, consisting of a simple optical fibre surrounded by glass, is unfortunately not usable for the entire range of black products. Indeed, the systematic heating of the sample to 150° C., in addition to the safety problems, can result in, for certain types of black products, degradations detrimental to the measurement of the flocculation threshold. The time taken for an analysis, is relatively long since it can take more than 5 hours.

Another method is also proposed for measuring the S value on black products with a "Porta" device, manufactured by the Finnish company FMS (Finnish Measurement Systems Ltd), and marketed by the English company Med-Lab. This instrument uses a continuous flow measuring cell for the sample to be analysed with optical detection of the flocculation threshold by means of a prism operating in total reflection. The measurement range is very wide and a result is always available, even with black products whose flocculation threshold is deemed difficult to measure. However, these results are obtained after modifications of the operating parameters of the method, which then become a function of the nature of the product, which is unacceptable when the range of products to be analysed is very variable, as in the oil industry.

Document FR2655909 describes a device for detecting a product suspended, emulsified or in the form of microbubbles in a liquid absorbing visible light. This device makes it possible to detect the beginning of the precipitation of asphaltenes in oil. It comprises a bundle of optical fibres, one part of which is used for emission and the other part for detection. A window near the end of the optical fibres isolates them from the medium to be studied. A mirror immersed in the medium to be measured reflects the light beam emitted towards the optical fibres used for detection. The device further comprises means for adjusting the distance separating the window from the mirror to avoid saturation or to obtain the strongest possible signal. This device is thus an indirect transmission device (presence of the mirror) and requires varying the optical path to avoid saturation and obtain the strongest possible detection signal.

Document U.S. Ser. No. 10/422,782B2 relates to the detection of contaminants in water by reacting the contaminant with a reagent which induces a colour change and/or fluorescence. The device allows measurement by absorbance and fluorescence. The system itself comprises a light emitter and a light detector that directly receives the emitted light after it has passed through the sample. It is planned to modulate the light source at a fixed frequency the principle of which consists in supplying the transmitter during a short period and watching the value on the receiver only during this period, hence the use of a demodulator configured in "lock in amplifier". The acquisition of the detected signal is thus carried out synchronously with the transmitter and is blocked the rest of the time. The aim here is to limit the sensitivity to noise and mainly that generated by ambient light and not to modulate the energy intensity of the transmitter as in the present invention.

The document WO2005003754A2 describes an automatic dosing device for determining the incompatibility of oil products. The detection system consists of a fibre optic light transmission spectrometer, the liquid to be measured passing through a 100 μm thick optical cell which is not detailed. The instrument is equipped with a circuit connected to various chambers and pumps allowing the introduction of a petroleum product, an aliphatic solvent, an aromatic solvent and an auxiliary solvent into a thermostatically controlled mixing container used for the dosage. The sample measurement time is 1 to 2 hours.

The publication "Flocculation Onset Titration of Petroleum Asphaltenes" (Energy & Fuels, 1999, 13, pages 315-322) studies the flocculation of asphaltenes by automatic dosing using in particular a Beckmann spectrometer.

There is now a standard (ASTM D7157-18-Revision 2018) for the determination of S, Sa, So values, which can be implemented by means of a device and a method described in document EP1751518 B1.

Document EP1751518 B1 describes a method for measuring the flocculation threshold wherein at least two light emitting and receiving probes are introduced into the medium to be measured, these probes operate by optical transmission at detection areas of distinct dimensions. It is then determined which of the two probes is suitable for the measurement by determining the transmission threshold of the medium before the addition of aliphatic solvent. Finally, the flocculation is determined with the aid of the probe thus designated after adding the amount of aliphatic solvent necessary for flocculation. In particular, one of the probes operates in indirect transmission by reflection. The method and device described allows the selection of the most suitable probe for the measurement from various probes introduced into the same medium, in particular after the addition of aliphatic solvent. Thus, the device can be switched from one probe to another after adding solvent. These probe changes, which correspond to changes in the optical path travelled by the light beam between a transmitter and its receiver, are simple and rapid but can cause signal oscillation phenomena that can lead to errors in determining the flocculation threshold. The company ROFA® markets a probe with an adjustable optical path length (SVA-130® probe) which could avoid such oscillations. However, changing the optical path length requires the intervention of an operator, which considerably increases the measurement time.

The methods currently proposed for measuring the flocculation threshold of asphaltenes in hydrocarbon products therefore have a certain number of drawbacks. They do not necessarily offer the simplicity, speed and precision required for the results, in particular for continuous control of a processing unit, for example visbreaking and/or an efficient mixing unit. Nor do they allow the direct analysis of a wide range of products according to their asphaltene content. They use techniques that cannot be easily automated and/or are not very easy to use.

The present invention aims to remedy one or more of the drawbacks mentioned above.

SUMMARY OF THE INVENTION

The invention relates to a device for measuring the flocculation threshold of a colloidal medium by the addition of an aliphatic solvent, comprising:
- at least one measuring cell operating by direct optical transmission and having a measuring chamber intended to receive the medium, and, associated with each measuring cell:
  - a light emitter emitting a light beam entering the measuring chamber along an emission direction,
  - a photoelectric light receiver directly receiving the light beam exiting from the measuring chamber, the receiver being able to deliver a current when it receives a luminous flux, a control system comprising:
  a light emitter control system configured to vary the luminous intensity of the light beam emitted between a minimum and a maximum value,
  a system for measuring the current delivered by the light receiver comprising:
    a current-to-voltage converter receiving the current delivered by the light receiver and delivering a voltage, this converter comprising a controlled switch distributing the current in a circuit selected from at least two impedance circuits having different impedances,
    a variable gain amplifier receiving the voltage delivered by the current-to-voltage converter and outputting a voltage,
    an analogue-to-digital converter receiving the voltage output from the variable gain amplifier and outputting a digital signal representative of the amount of current delivered by the light receiver,
    a control management system for each measuring cell, configured to control the light emitter control system, the current-to-voltage converter switch and the variable gain amplifier of each control system.

This configuration of the control and management system makes it possible to modulate the luminous intensity of the light beam emitted by the transmitter according to the medium to be measured and to select an amplitude range of the signal received in the detection areas of the analogue-to-digital converter of the measuring system. Thus, it is possible to modulate the measurement range of the signal and to obtain detection, without saturation, for any type of light or dark sample.

The measuring device according to the invention has the advantage of allowing the measurement of very light to very dark samples without requiring a modification of the optical path, either by moving parts of the measuring cell or by using separate cells with different optical paths.

In addition, the measuring cell operates by direct optical transmission, in other words the light beam emitted by the transmitter is received directly by the receiver, without any intermediate optical reflection device.

In particular, advantageously, each measuring cell can thus have a measuring chamber defined by fixed walls, two opposite walls of which form optical elements capable of being traversed by a light beam. Consequently, the optical path length of the measuring cell is fixed, the measuring cell therefore has no moving parts, the transmitter and the receiver being fixed. In general, the transmitter and the associated detector are advantageously located outside the measuring chamber, each facing an optical element of the measuring chamber.

Thus, only one probe is necessary to measure more or less dark products which consequently allow more or less of the emitted light beam to pass through, which makes it possible to avoid the oscillations observed with the device described in document EP1751518 B1.

The use of a management system makes it possible to automate the operation of the device and thus to dispense with an operator.

It should be noted that the management system can be connected to other components of the device and arranged to control them, such as temperature sensors, one or more members for regulating the temperature of the medium, or solenoid valves, or even members for circulating fluids, in order to control the distribution of fluids and possibly their circulation, particularly when the device comprises a circuit as described below.

The transmitter control system allows luminous intensity of the light beam to be varied, in other words the amount of light emitted in the emission direction. With regard to a transmitter that can emit in the infrared or near infrared, it should be understood that "luminous intensity", is a misuse of the term for energy intensity, namely a radiometric quantity that is the measure of the power (or energy flow) of electromagnetic radiation emitted by a quasi-point source, per unit solid angle, in a given direction. Its unit in the international system is the watt per steradian (W sr$^{-1}$). In particular, the variation in the luminous intensity mentioned above is the variation in energy intensity (the power radiated in the emission cone) obtained by varying the electric current through the emitter. When the emitter is a light emitting diode, the energy intensity is almost proportional to the electric current flowing through the diode.

Advantageously, the control system can allow the luminous intensity to be varied in very small increments.

This system for controlling the luminous intensity emitted can advantageously be a system for controlling the intensity of the current supplying the transmitter. The transmitter is typically supplied with direct current, the intensity of which can be varied.

It should be noted that the step of variation of the intensity of the current supplying the transmitter can be chosen by the skilled person according to the desired measurement accuracy for the products to be measured. In particular, the lower the variation step, the greater the measurement accuracy, especially on clear products. For example, the intensity of the current supplying the emitter can be varied in a range from a few microamperes to 100 mA, for a light emitting diode type.

This control system for example may comprise, or consist of, a digital-to-analogue converter. The number of bits in the digital-to-analogue converter can be chosen according to the desired current variations: the greater the number of bits, the lower the current variation step. For application to the measurement of hydrocarbon products containing asphaltenes, for example a digital-to-analogue converter with at least 16 bits can be used.

Depending on the current range of the transmitter, the control system can be configured to vary the current in steps of 1 to 2 µA.

The variable gain amplifier can have a number of gains from 0 to a maximum value G, in powers of 2, with a gain equal to 0 corresponding to the absence of modification of the amplitude of the received and delivered voltages, a gain G corresponding to a delivered voltage having an amplitude G times greater than the amplitude of the received voltage. For example, the gain may vary from 0 to 128 and thus take the values of 0, 2, 4, 8, 16, 32, 64 and 128.

Advantageously, for a simple implementation, the variable gain amplifier can be integrated into the analogue-to-digital converter. In particular, the analogue-to-digital converter can form a variable gain amplifier. The number of bits in the analogue-to-digital converter can be chosen according to the desired resolution. For example, a 16- or 24-bit analogue-to-digital converter can be used for the measurement of hydrocarbon products containing asphaltenes.

Advantageously, the impedance of each impedance circuit of the current-to-voltage converter can be selected so that, in a range of current intensities, the voltage delivered by one of the impedance circuits has an amplitude range intersecting the amplitude range of the voltage delivered by another impedance circuit. This allows all operating areas to be covered.

In a preferred embodiment, only two impedance circuits may be provided. This makes it possible to limit the electronic components and the disturbances they may cause. However, more impedance circuits could be provided as required.

Each measuring chamber may have two fixed optical elements forming opposite walls, the minimum distance separating the two optical elements in the emission direction having a value in the range of 0.4 to 1.2 mm, preferably of 0.5 to 1 mm. Such a distance is particularly suitable for measuring a wide variety of hydrocarbon samples, from very light to very dark, in particular samples containing asphaltenes.

The emitter and receiver of each measuring cell may have a light beam outlet opening and a sensitive area respectively. Advantageously, the said outlet opening and the said sensitive area can each be positioned within a housing which is impervious to light rays coming from outside the measuring cell, each housing only opening onto the measuring chamber, onto opposite walls thereof, in particular onto walls forming optical elements capable of being crossed by a light beam. This improves the measurement accuracy, especially for dark samples.

Advantageously, the measuring device may comprise at least one temperature sensor and at least one temperature control member connected to the management system and the management system may be arranged to control the temperature of the medium.

Advantageously, each measuring cell may comprise a fluid inlet and outlet connecting the measuring chamber to an associated fluid circuit equipped with a fluid flow member. In other words, each measuring chamber of a measuring cell forms part of a fluid circuit specific to the measuring device according to the invention, which is not in communication with other fluid circuit(s).

Such a fluid circuit can be formed by one or more lines connected to each other.

In particular, each fluid circuit may further comprise one or more of the following:
- at least one tank and at least one liquid injection line connected to each tank, optionally connected to the circuit by a valve, in particular a solenoid valve,
- a mixing chamber with an inlet and an outlet connected to the fluid circuit,
- at least one temperature control member.

This temperature control member may be chosen from a heat exchanger, a heating resistor, a Peltier effect device or other.

Advantageously, the fluid circuit can form a closed loop within which the medium circulates.

The measuring device according to the invention allows the measurements to be carried out in a very short time, making continuous measurements possible.

Also, advantageously, the device may comprise means for continuously injecting liquid, in particular at a constant flow, into the fluid circuit, in particular into the lines of the fluid circuit. This allows continuous injection of the aliphatic solvent into the circuit. Such a continuous injection while the liquid circulates within the circuit makes it possible to obtain rapid homogenization of the mixture. Due to the very short measurement time, a measurement can be made with the measuring cell while the liquid is circulating in the fluid circuit, without ceasing to add the solvent, which is injected at a constant low flow. This homogenisation will be all the faster as the solvent is injected within the lines of the circuit. These injection means may comprise an injection line, a pump and a solenoid valve.

The device according to the invention may have two or three identical measuring cells, each associated with a transmitter, a receiver and a control system, each cell being connected to its own fluid circuit. The measuring cell control systems can be controlled by the same management system.

The invention also covers a method for measuring the flocculation threshold of a colloidal medium by adding an aliphatic solvent using the device according to the invention, comprising the step of determining, with the aid of the measuring cell of said device, the flocculation threshold after the addition of the amount of aliphatic solvent necessary for flocculation.

The invention also provides a method for measuring the flocculation threshold of a colloidal medium by the addition of an aliphatic solvent, in particular paraffinic, comprising the following steps:

(i) the medium is introduced into a measuring chamber of a measuring cell operating by direct optical transmission, the measuring cell forming part of a device for measuring the flocculation threshold further comprising, associated with the measuring cell:
- a light emitter emitting a light beam entering the measuring chamber along an emission direction,
- a photoelectric light receiver directly receiving the light beam exiting from the measuring chamber, the receiver being capable of delivering a current when it receives a luminous flux,
- a control system comprising:
- a light emitter control system configured to vary the luminous intensity of the emitted light beam between a minimum and a maximum value,
- a system for measuring the current delivered by the light receiver comprising:
  - a current-to-voltage converter receiving the current delivered by the light receiver and delivering a voltage, this converter comprising a controlled switch distributing the current in a circuit selected from at least two impedance circuits having different impedances,
  - a variable gain amplifier receiving the voltage supplied by the current-to-voltage converter and delivering a voltage equal to or proportional to the incoming voltage,
  - an analogue-to-digital converter receiving the voltage output from the variable gain amplifier and outputting a digital signal representative of the amount of current delivered by the light receiver,
the measuring device further comprising a control management system configured to control the light emitter control system, the current-to-voltage converter switch and the variable gain amplifier, (ii) using the management system, a luminous intensity of the light beam emitted from the transmitter is set, the switch of the current-to-voltage converter is controlled to select an impedance circuit and a gain of the variable gain amplifier is selected so as to obtain a signal detectable by the analogue-to-digital converter, (iii) the flocculation threshold is determined with the aid of the measuring device after the addition of the amount of aliphatic solvent required for the flocculation, optionally the gain of the variable gain amplifier of the measuring device is modified during the addition.

This method can be implemented by the device of the invention, in particular for each measuring cell of the device of the invention.

Advantageously, during the measurement, the luminous intensity of the light beam and the impedance circuit are not changed, only the gain can be adjusted. A step to adjust the luminous intensity emitted by the transmitter, the impedance circuit and the gain can then be planned before the start of the measurement. In particular, before the start of the measurement, it is advantageous to set the gain to a maximum or a non-minimum value, which can then be reduced as the sample is diluted and clarified.

The device for measuring the flocculation threshold according to the invention makes it possible to carry out measurements in a very short time, to the order of a few microseconds, allowing measurements to be taken while the aliphatic solvent is being added. Thus, advantageously, during step (iii), the aliphatic solvent can be added continuously and the measurements are carried out using the measuring device while the aliphatic solvent is being added. In particular, the aliphatic solvent can then be injected into a fluid circuit, in particular into fluid lines, the fluid circuit being connected to the measuring chamber of the measuring cell, this fluid circuit being equipped with a fluid flow member.

Advantageously, these continuous measurements can be carried out at a constant flow of aliphatic solvent.

Advantageously, the probes can be probes emitting in the NIR range and the occurrence of flocculation is identified by determining the absorption peak.

Advantageously, the process can be implemented at a predetermined adjustable temperature, for example by means of a temperature control member. This may allow the product to be heated, for example to facilitate its dissolution, prior to the addition of the aliphatic solvent, but to perform the measurement at a predetermined lower temperature. For example, the measurement could be carried out at a temperature of 15 to 60° C.

Advantageously, the process may comprise a step of diluting (ii) the colloidal medium with a predetermined amount of aliphatic solvent prior to step (i).

According to one embodiment, the colloidal medium comprises asphaltenes.

The invention further provides a method of determining the stability of a mixture comprising asphaltenes by implementing the method of measuring the flocculation threshold of a colloidal medium at least twice according to the invention on a medium containing the mixture and a given amount of aromatic solvent, at different dilution rates. The process for measuring the flocculation threshold can be in particular implemented at least twice in succession in the same measuring cell of a measuring device or simultaneously in two or more identical measuring cells of the same measurement device.

According to one embodiment, the aromatic solvent/ aliphatic solvent pair (in particular paraffinic) used is the toluene/n-heptane pair.

The different embodiments previously described as well as those described with reference to the figures may be combined.

DETAILED DESCRIPTION OF THE EMBODIMENTS OF THE INVENTION

Figure 1:
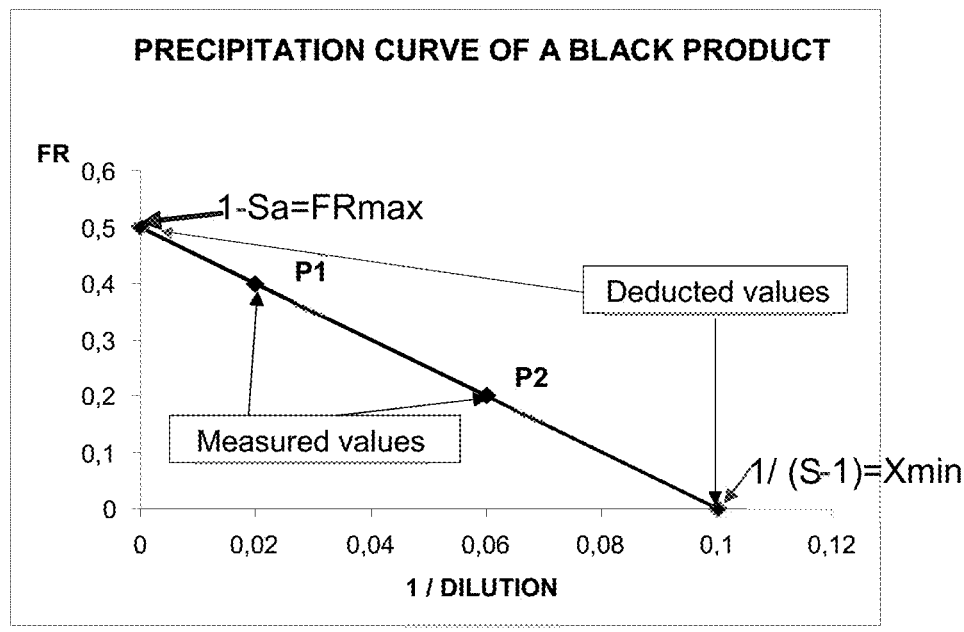
FIG. 1 is a representation of the aromaticity graph of the solvent as a function of the inverse of the dilution, i.e. the precipitation curve of a black product which, at a given dilution rate of this same black product, associates the minimum aromaticity of the solvent necessary so that the mixture does not precipitate.

With reference to FIG. 1, the method is described using the device described in document EP1751518 B1 for determining the values of S, So and Sa, for a given black product mixture.

The intrinsic stability of any colloidal system is quantified by a dilution using a paraffinic solvent of a black product, such as a fuel oil, atmospheric (or under vacuum) oil distillation residue, crude oil, previously mixed with an aromatic solvent. This intrinsic stability (S) depends on the aromatic characteristics of the asphaltenes (Sa) and the aromatic characteristics of the medium (So), as described above. The intrinsic stability S of a colloidal system is determined by measuring the flocculation threshold of at least 2 different mixtures. From at least these 2 points, a straight line is drawn, known as the precipitation of a black product (FIG. 1), which allows access to the parameters Sa and S, then by calculation, to the value So.

By adding a paraffinic solvent to the black product, the mixture becomes unstable from a certain dilution rate X min., called "minimum dilution rate".

The following definitions are used, as defined in the ASTM D7157-18 standard (Revision 2018):

Dilution rate X (ml/g):
volume of total solvent (aromatic+paraffinic) in millilitres/mass of black product in grams.

intrinsic stability S of the black product:
S=1+Minimum dilution rate. Here we find the notion of S−1 as a stability reserve.

For the experimental measurements, two types of solvents are used, the first is aromatic, consisting essentially of aromatic molecules for the dilution of the sample (for example toluene, xylene, or even 1-methylnaphthalene) and the second is an aliphatic paraffinic solvent (for example n-heptane, cetane, or even iso-octane) to cause flocculation of the asphaltenes.

The flocculation rate FR ("flocculation ratio") is defined as follows:

FR=volume of aromatic solvent/total volume of solvent.

The ability of asphaltenes to be peptised ("peptisability of an asphaltene") is defined by: Sa=1−FRmax, where FRmax is the maximum flocculation rate (at 1/X=0).

The precipitation curve is the function of the flocculation rate FR as a function of the dilution rate, here:

$$1-Sa=f(1/X)=A+B/X.$$

A and B are constants that depend only on the sample and allow access to the values of S, So and Sa.

We proceed as follows. We start from a first mixture of a given mass of black product in a given quantity of aromatic solvent and we add in successive increments a paraffinic solvent. The flocculation threshold is determined (in particular by a method using an IR probe) and the dilution rate and the flocculation rate FR associated with the analysed mixture are noted. A first point is obtained, identified by point P1 on the graph (FIG. 1). The operation is repeated, with a starting product that is initially less strongly diluted in the aromatic solvent. This results in another measurement materialised by point P2. With the two points P1 and P2 it is then possible to draw the straight line passing through these points and to obtain limit values (1−Sa) on the y-axis (FRmax or infinite dilution rate) and 1/(S−1) on the x-axis (FR zero). It then becomes possible to access the values of S, Sa then So by calculation.

This technique, which refers to the ASTM D7157-18 standard (Revision 2018), and which consists of the construction of a precipitation curve, from at least two measurement results (three in the standard), to then determine the values of the borderline and null aromatics, is generally followed in the invention. The masses, volumes and products used are conventional in the art of this type of analysis.

With reference to FIG. 2 and FIGS. 3 to 5, the device (1) according to the invention comprises a measuring cell (10) operating by direct optical transmission and having a measuring chamber (101). This measuring chamber is of fixed dimensions, defined by fixed walls.

The device (1) also comprises, associated with the measuring cell (10), a light emitter (12) emitting (configured to emit) a light beam entering the measuring chamber (101) along an emission direction (D) and a light receiver (14) directly receiving the light beam exiting from the measuring chamber (101). In other words, the light receiver (14) is positioned to directly receive the exiting light beam. In particular it can be positioned in the emission direction (D), on one side of the measuring chamber (101) opposite the side where the light emitter (12) is located, as shown in the figures. The emitter for example is a conventional IR emitter, for instance a light-emitting diode. The emitter (12) may preferably be chosen so that its emission spectrum is constant whatever the luminous intensity it emits, in other words whatever the intensity of the electric current which supplies it. For example, a light-emitting diode based on aluminium gallium arsenide may be used.

The receiver (14) is a photoelectric receiver capable of delivering a current when it receives a luminous flux.

Figure 3:
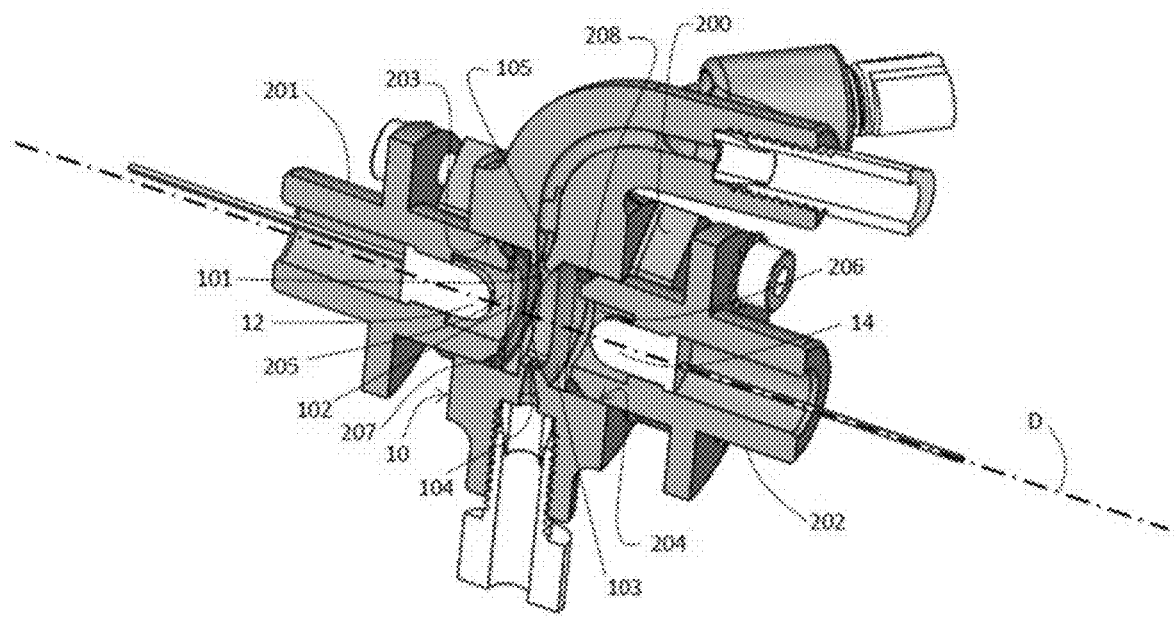
FIG. 3 is a schematic representation in perspective and cross-section of a measuring cell according to one embodiment of the device of the invention.

In the example shown in FIG. 3, the measuring cell (10) comprises a fluid inlet (104) and an outlet (105) in fluid communication with the measuring chamber (101).

In the embodiment shown, unlike the existing conventional probes, the measuring chamber (101) is part of the measuring cell (10) but is not defined by the transmitter (12) and the receiver (14) although that it is located between the latter allowing the light beam to pass through the measuring chamber. The measuring chamber (101) is defined here by fixed walls including two opposite walls forming optical elements (102, 103) capable of being traversed by a light beam.

A first optical element (102) located on the side of the emitter (12), in this case a plate with parallel sides, allows the transmission of the light beam from the emitter (12) to the sample located within the measuring chamber (101). A second optical element (103) located on the side of the detector (14), in this case a plano-convex spherical lens, makes it possible to focus the light beam transmitted by the sample onto the detector (14).

Other pairs of optical elements than those previously listed can be considered, however, the configuration shown in the example has the advantage of being particularly efficient.

In particular, the two optical elements may be selected from a parallel-sided plate and an aspherical lens, two parallel-sided plates, a parallel-sided plate and a spherical lens, preferably a parallel-sided plate and a spherical lens.

It should be noted that each of the optical elements (102, 103) can be a spherical lens, a parallel-sided plate or an aspherical lens. These different optical elements can be made of glass, polymer, metalloid, but also of hybrid material (glass/polymer).

The measuring cell (10) can be made of polymer material and formed for example of a body (200) defining the inlet (104), the outlet (105) and the walls of the measuring chamber (101) which are not formed by the optical elements (102), (103). The transmitter (12) and the receiver (14) in this case each arranged within a support (201), (202), here in a cylindrical shape with mounting flanges, inserted into corresponding holes (203), (204) of the body. These supports (201), (202) are located on either side of the measuring chamber (101) along direction D. These supports (201), (202), when attached to the body (200), hold the optical elements (102) and (103), inserted at the bottom of the holes (203), (204) in a facing position within the body. O-rings (207, 208) arranged between each optical element (102, 103) and the support (201, 202) which holds it in position makes it possible to seal the measuring chamber (101) and to ensure that the optical elements are well maintained.

The measuring chamber (101) can be in the form of a pipe open at both ends, with a closed cross-section.

The invention is of course not limited by a particular shape of the measuring cell, provided that the walls of the measuring chamber are fixed and that the transmitter and the receiver are located outside the measuring chamber. In general, the measuring cell used in the present invention does not contain any mobile or movable component, including the transmitter and the receiver.

Preferably, the distance between the optical elements (102), (103) should be sufficiently low to allow the detection of very dark samples. Advantageously, for hydrocarbons likely to contain asphaltenes, the minimum distance separating the two optical elements in the emission direction D can be set at a value within the range of 0.4 to 1.2 mm, preferably 0.5 to 1 mm.

Figure 4:
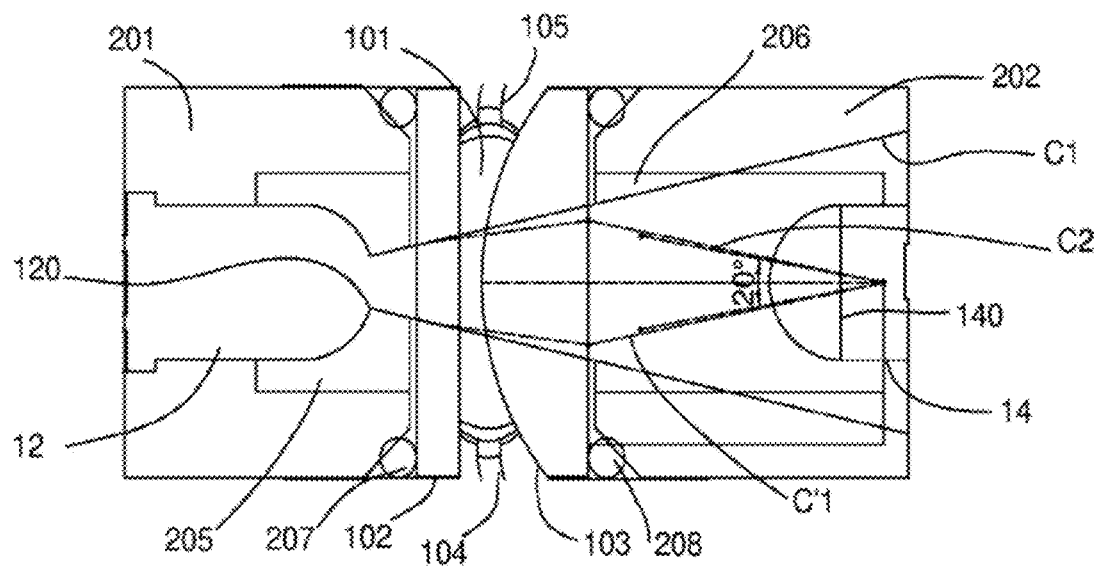
FIG. 4 is a cross-sectional schematic representation of a part of the measuring cell in FIG. 3.

FIG. 4 schematically represents the path travelled by the light beam according to one embodiment. In this Figure, the receiver (14), and more precisely its sensitive area, is positioned at the theoretical focal point of the optical system, the optical elements (102), (103) of the measuring chamber (101) being separated by a distance chosen in the value range from 0.4 to 1.2 mm.

In this example, the emission cone C1' of the transmitter (12), corresponding to the light beam cone C1 emitted by the transmitter after it has passed through the two optical elements (102, 103), here has a half angle at the apex of 10 to 15°, the half angle at the apex of the C2 receiving side of the receiver (14) being 10°. It should be noted here that the reception cone is entirely contained within the light emission cone of the transmitter, and does not leave it.

A person skilled in the art can advantageously configure the measuring cell so that the emission cone C1 of the transmitter illuminates a sufficient volume of the measuring chamber (101) so that the amount of product illuminated by this emission cone C1 is homogeneous and representative of the product to be measured.

In the example shown, the transmitter (12) and the receiver (14) of each measuring cell have a respective light beam outlet opening (120) and a sensitive area (140), which are each respectively positioned within a housing (205, 206)

that is impervious to light rays coming from outside the measuring cell. Each housing (205, 206) only opens onto the measuring chamber (101), on the opposite walls thereof formed by the optical elements (102, 103). In other words, each housing (205, 206) is closed by an optical element (102, 103) of the measuring chamber (101). In the example, these housings (205, 206) are part of the supports (201, 202) described previously.

The device (1) also comprises a control system (16) and a management system (22) for the control system.

The control system (16) comprises a control system (17) of the light transmitter and a measurement system (18) for the current delivered by the light receiver.

The light emitter control system (17) is configured to vary the luminous intensity of the light beam emitted by the emitter (12) between a minimum and a maximum value. In the example shown, this is a system for controlling the amount of the current supplied to the transmitter. It may be advantageous to use a 16-bit digital-to-analogue converter. Such a converter makes it possible to finely modulate the variation in intensity of the electric current which supplies the transmitter (12). This modulation is based on the maximum number of points of the converter (here $2^{16}=65536$ points maximum). Such a dynamic range makes it possible to supply the transmitter with a very low current (for example of the order of a few micro-amperes for a number of points less than 200), corresponding to a low emitted luminous intensity, up to a high current (nearly 92 mA for the maximum number of points), and therefore maximum luminous intensity. The invention is of course not limited to this embodiment and software could be used to modulate the current intensity over a wide range with high accuracy or any other suitable device. The use of a 16-bit digital-to-analogue converter nevertheless has the advantage of being simple and robust. Of course, a converter with more bits could be used. It should be noted that the control system supplies a direct current to the transmitter and not a pulsed current.

Figure 5:
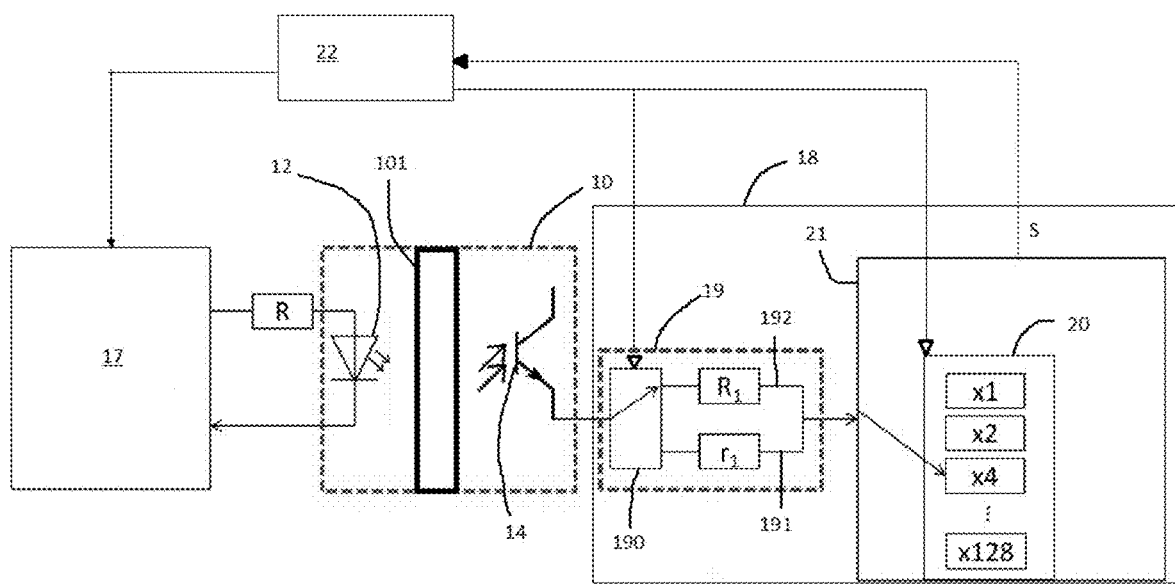
FIG. 5 is a schematic representation of a control system for a measuring cell.

As shown in FIG. 5, the measurement system (18) comprises a current-to-voltage converter (19), a variable gain amplifier (20) and an analogue-to-digital converter (21).

The current-to-voltage converter (19) receives the current supplied by the receiver (14) and outputs a voltage. This converter (19) comprises a controlled switch (190) distributing the current in a circuit selected from at least two impedance circuits with different impedances. In the Figure, the current-to-voltage converter (19) has a first impedance circuit (191) with an impedance r1 and a second impedance circuit (192) with an impedance R1, greater than the impedance r1. The current-to-voltage converter (19) thus makes it possible to obtain two measurement ranges. When the sample to be measured is clear, in other words has a low light absorption, the management system (22) can be configured to control the switch (190) and distribute the current to the first low impedance circuit (191) in order to avoid saturating the downstream analogue-to-digital converter (21). Conversely, when the sample to be measured is dark, in other words strongly absorbing light, the management system (22) can be configured to control the switch (190) and distribute the current to the second higher impedance circuit (192) to generate a voltage detectable by the downstream analogue-to-digital converter (21).

The voltage delivered by the current-to-voltage converter (19) then enters the analogue-to-digital converter (21) via the variable gain amplifier (20). The latter thus receives the voltage delivered by the current-to-voltage converter (19) and in turn delivers a voltage equal or proportional to the incoming voltage. The variable gain amplifier (20) has various gains (here from 0 to 128 in powers of 2) which act as additional measurement ranges. At the start of the measurement, the management system (22) can be configured to select a sufficiently high, and preferably not minimal, gain and to, during the course of the measurement, reduce this gain to avoid saturation of the analogue-to-digital converter (21) as the test product is diluted. The person skilled in the art will thus be able to determine the number of gains necessary according to the products to be tested, so that the voltage delivered by the variable gain amplifier (20) is always within the operating range of the analogue-to-digital converter (21) used.

Finally, the analogue-to-digital converter (21) receives the voltage delivered by the variable gain amplifier (20) and delivers a digital signal S representative of the amount of current supplied by the receiver (14). An analogue-to-digital converter (21) with high resolution, for example at 24 bits, should be preferably chosen. Of course, an analogue-to-digital converter with a different number of bits can be considered.

The management system (22) of the control system (16) is configured to control the light emitter control system, the current-to-voltage converter switch and the variable gain amplifier. This allows for an automation measurement.

This management system (22) may comprise one or more processors of the microprocessor, microcontroller or other type, for example forming part of a computer. In particular the processor(s) comprise(s) of a computer program execution means suitable for implementing the method described in the present invention.

In one embodiment, the management system can be arranged to receive data. The management system can also be arranged to transmit data, particularly to a display device such as a screen. The management system can thus comprise one or more input, output, or input/output interfaces. These can be wireless communication interfaces (Bluetooth, WI-FI or other) or connectors (network port, USB port, serial port, Firewire® port, SCSI port or other).

In one embodiment, the management system may include storage means which may be a random access memory or a RAM memory (from the English "Random Access Memory"), an EEPROM (from the English "Electrically-Erasable Programmable Read-Only Memory"), a flash memory, an external memory, or other. These storage means can in particular store the data received, and possibly computer program(s).

The management system (22) is configured for example to control the parameters of the control system according to the opacity of the tested product. This servo control will therefore depend on:
- of the luminous intensity emitted by the transmitter,
- of the selected impedance circuit,
- of the gain of the variable gain amplifier,
- of the initial value of the digital signal generated by the analogue-to-digital converter.

This servo control can be configured to modulate the amplitude of the voltage entering the analogue-to-digital converter in order to reach a setpoint value corresponding to a minimum value measurable by the converter.

In a known manner, an analogue-to-digital converter can detect a voltage in a determined detection range: below the minimum value of this range, no signal is generated, above the maximum value of the range, saturation of the converter causes a loss of sensitivity. The setpoint value is generally chosen in a part of the detection range close to the minimum value.

The management system for example can be configured to perform an adjustment of the measuring device during an adjustment step.

As an example, this adjustment step can be carried out according to the program steps described below.

STEP 0 (initial step): the impedance circuit with the lowest impedance is selected, the highest gain is selected, the luminous intensity emitted by the transmitter is adjusted to a value close to its minimum value and the value of the signal S delivered by the analogue-to-digital converter is recorded.

STEP 1: the recorded signal S is compared with a setpoint value.

If the value of signal S is lower than the setpoint value, we go to STEP 2.

If the value of signal S is greater than the setpoint value, we go to STEP 3.

If the value of the signal S is equal to the setpoint value, we go to STEP 4.

STEP 2: the luminous intensity emitted by the transmitter is increased until the setpoint value of the signal S generated by the converter is reached or until the maximum luminous intensity of the transmitter is reached.

If the setpoint value of signal S is reached, we go to STEP 4.

Otherwise, we go to STEP 5.

STEP 3: the luminous intensity emitted by the transmitter is reduced until the setpoint value of the signal S generated by the converter is reached or until the minimum luminous intensity of the transmitter is reached.

If the setpoint value of signal S is reached, we go to STEP 4.

Otherwise, we go to STEP 9.

STEP 4: the luminous intensity value, the chosen impedance circuit and the gain are recorded and we go to STEP 10.

STEP 5: change the impedance circuit and select the higher impedance circuit, record the signal value and go to STEP 6.

STEP 6: the recorded signal S is compared to the setpoint value.

If the value of signal S is lower than the setpoint value, go to STEP 7.

If the value of signal S is greater than the setpoint value, go to STEP 8.

STEP 7: the luminous intensity emitted by the transmitter is increased until the setpoint value of the signal S generated by the converter is reached.

When the setpoint value of the signal S is reached, go to STEP 4.

STEP 8: The luminous intensity emitted by the transmitter is reduced until the setpoint value of the signal S generated by the converter is reached or until the minimum luminous intensity of the transmitter is reached.

If the set value of signal S is reached, go to STEP 4.

Otherwise, go to STEP 9.

STEP 9: The gain value is reduced until the setpoint value of the signal S generated by the converter is reached.

When the setpoint value of the signal S is reached, go to STEP 4.

STEP 10: End of the programme.

The setpoint value corresponds for example to a minimum value measurable by the converter (21).

Figure 2:
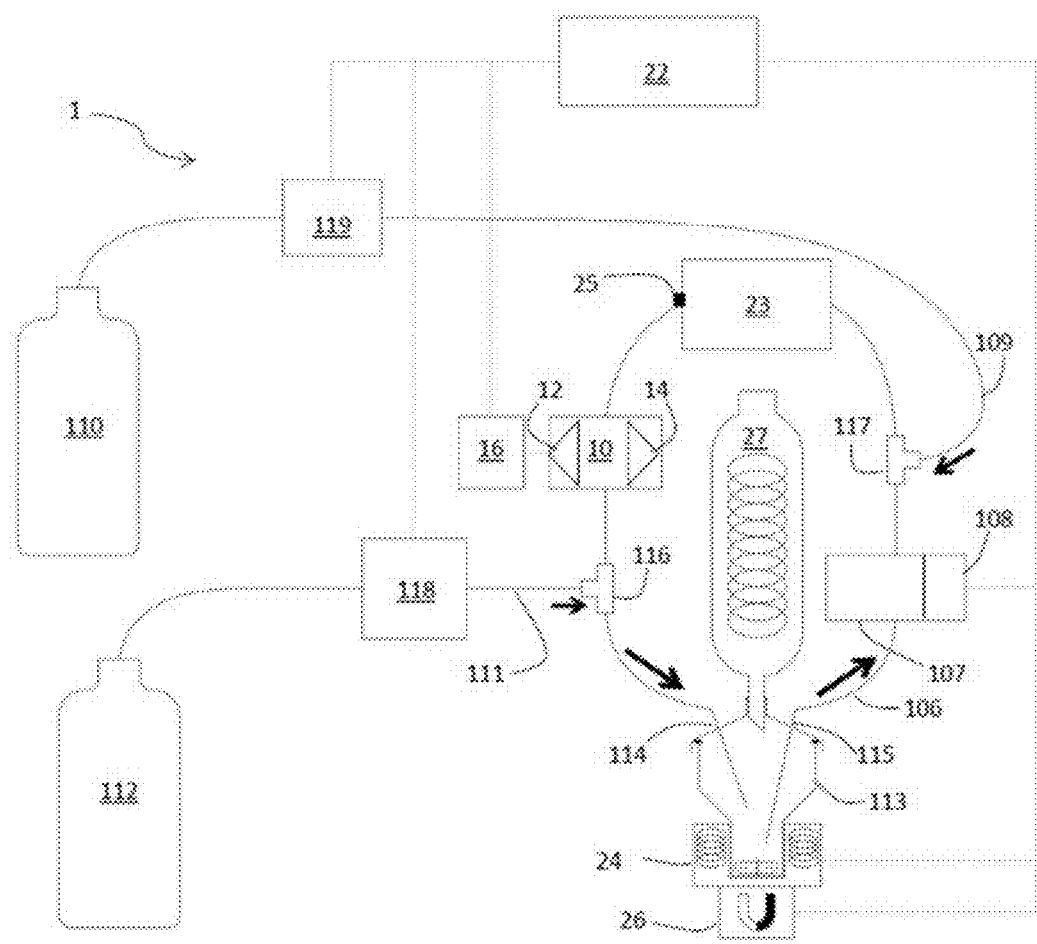
FIG. 2 is a schematic representation of a device according to one embodiment of the invention.

In the embodiment shown, as seen in FIG. 2, the device (1) further comprises a temperature control member (23) located upstream of the measuring cell (10) in relation to the fluid flow, in this case a Peltier effect device which can be a cooling or heating member depending on the direction of the electric current passing through it. It also comprises one or more temperature sensors (25), for example a temperature sensor located upstream of the measuring cell, in this case at the output of the temperature control member. A temperature sensor may also be provided at the level of a mixing chamber (113), at the inlet or at the outlet thereof, or even integrated into a thermostat unit (24) surrounding this mixing chamber, as represented. This thermostat unit (24) forms another temperature control member here dedicated to heating. These components can be controlled by the management system (22) which can then be arranged to automatically manage the temperature of the medium. It should be noted that any other suitable device for temperature control may be used.

The measuring cell (10) could be immersed in the medium so that the latter completely fills the measuring chamber. However, preferably, as shown in FIGS. 2 to 4 and already described, the measuring cell (10) comprises a fluid inlet (104) and a fluid outlet (105) connecting the measuring chamber (101) to a fluid circuit (106), which is equipped with a fluid flow member (107), in this case a peristaltic pump (107) controlled by a stepping motor (108).

Specifically, in the example, the fluid circuit (106) comprises:
- a first liquid injection line (109) connected to a tank (110) for injecting the first solvent, for example the aromatic solvent,
- a second liquid injection line (111) connected to a second tank (112) for injecting the second solvent, for example the paraffinic solvent,
- a mixing chamber (113) having an inlet (114) and an outlet (115) connected to the fluid circuit (106), for receiving the medium,
- the temperature control member (23) and the heating member (24) as mentioned above.

The injection lines (109) and (111) can be equipped with solenoid valves (116), (117), and pumps (118), (119) which are preferably controlled by the management system (22) for the automation of the device.

The fluid circuit (106) here forms a loop which can therefore be closed for the circulation of the medium within the loop, for example in the direction of circulation symbolised by the arrows in FIG. 2.

A reflux column (27) may be provided to allow the product contained in the chamber to be heated under reflux in order to facilitate the dissolution of the sample.

The operation of the device according to the invention is described below.

The sample to be analysed is introduced into the measuring chamber of the measuring cell of the device according to the invention. In the device represented, the sample is introduced into the mixing chamber before being circulated through the circuit and into the measuring chamber. In particular, the product volume is sufficient to completely fill at least the measuring chamber. For example, the volume of the measuring chamber can represent $\frac{1}{10}$th of the total volume of the circuit.

In the example, this introduction step is followed by a step of adding the aromatic solvent to the product to form the medium to be analysed. The sample is then diluted by the aromatic solvent before circulating within the measuring chamber of the measuring cell.

This is followed by an adjustment step during which the luminous intensity emitted by the transmitter is set, the impedance circuit and the gain are selected, as previously described. This adjustment step, carried out before the addition of paraffinic solvent, i.e. before flocculation, makes it possible to obtain a signal that can be detected by the receiver. It is possible, for example, to implement the adjustment step as described above. By detectable signal, it is meant a signal that can be distinguished from background noise and which is not saturated.

Finally, the flocculation is determined with the aid of the measuring device, after the addition of the amount of paraffinic solvent required for flocculation. To this end, the paraffinic solvent is gradually added and the drop in transmission corresponding to the flocculation of the asphaltenes is noted. This determination is done by conventional techniques, for example, by measuring the absorption peak.

In particular, the luminous intensity emitted by the transmitter and the impedance circuit remain fixed as the paraffinic solvent is diluted. If necessary, the gain can be reduced during dilution so as not to saturate the converter (21). When decreasing the gain to the lower gain value, the management system will be able to double the value of the signal S at the output of the converter (21) which will make it possible to avoid a variation in the signal amplitude due to the change of gain.

In this way, the signal can be measured with good accuracy with a single, appropriately adjusted measuring cell, which saves considerable time for the operator.

It should be noted that during the measurement, the luminous intensity emitted by the transmitter advantageously remains fixed, which is obtained by supplying a constant direct current to the transmitter.

The minimum value of the luminous intensity emitted by the transmitter corresponds for example to a value below which the accuracy of the measurement is too low to distinguish a signal from background noise.

According to one advantageous embodiment, implementing in particular the device described with reference to the figures, the introduction stage comprises a dissolution phase, during which the medium is introduced into the mixing chamber (113), in a sufficient quantity to completely fill the circuit (106), then the temperature of the medium is regulated to a dissolution temperature by means of the heating member (24). This dissolution phase is preferably carried out with stirring, in this case by means of a magnetic stirrer (26) located under the mixing chamber (113). The aromatic solvent is then injected into the mixing chamber (113) maintained under agitation.

This dissolution phase can optionally be followed by a pre-dilution phase with the paraffinic solvent, during which a predetermined quantity of this solvent can be injected into the circuit. This is done in the case of a very aromatic and stable product or when the product is too dark and the detector power reaches its maximum without having detected the flocculation volume.

A cooling phase is then carried out during which the temperature is regulated to a predetermined test temperature by means of the temperature control member (23).

This is followed by a dosing phase during which the paraffinic solvent is gradually added. This addition of solvent can be achieved by incremental or continuous addition. The signal from the converter (21) is then acquired and recorded either after each addition of solvent, or during the addition of solvent. In the latter case, the flow of solvent introduction into the circuit may be constant, for example of the order of 1 mL/minute. It should be noted that, in all cases, the product to be analysed circulates in the circuit during the addition of the solvent and the acquisition of the signal. This dosing phase can be stopped by an operator, when the maximum volume of the mixing cell has been reached or when a predetermined number of incremental additions has been made or when a predetermined volume of solvent has been added.

It is then possible to carry out a cleaning phase for example by circulating the aromatic solvent in the circuit.

The invention is described with reference to a device comprising a single measuring cell. It should be noted however that the device of the invention may comprise various identical independent measuring cells, for example three, in order to simultaneously perform three tests in parallel on a product.

In addition, the device according to the invention makes it possible to obtain a possible spectral range of application for the measurements which is very broad. The device according to the invention is suitable for determining the S, Sa and So values for all types of residues and fuels and is practically not limited as to the nature of the medium to be tested. As the device comprises only one type of measuring cell, it is possible to carry out various measurements in less time compared to devices that use a number of cells to measure the same product. It is possible to carry out 3 measurements with the same cell and therefore obtain 3 points of the curve and thereby a good repeatability of the measurements for S, Sa and So. Finally, the determination method according to the invention can be implemented at an ambient temperature or at a predetermined temperature, which makes it possible to measure the parameters S, Sa and So at a given temperature and to check their evolution as a function of temperature, since the stability of asphaltenes is temperature dependent.

In general, the aromatic solvent/paraffinic solvent pair used in the invention is the toluene/n-heptane pair.

EXAMPLES

The following examples illustrate the invention without limiting it.

Example 1

Measurements were carried out on samples of different black products for which the S, Sa values were measured and So calculated, on the one hand with a method using the SVA-130® probes proposed by the company ROFA implementing the method described in the ASTM D7157-18 standard (Revision 2018) ("Measurement Method A") and on the other hand with the device and the method in accordance with the present invention ("Measurement Method B").

The device according to the present invention is of the type described with reference to FIGS. 2 to 5. The measuring cell in particular comprises a parallel-sided plate and a spherical lens, the distance between the window and the lens being 0.7 mm at the centre and 2 mm at the edges.

The volume of the circuit loop here is 4 ml. The measurements are made while the fluid is circulating at a speed of approximately 10 mL/min. The test temperature here is room temperature, i.e. 21° C. It is possible to heat the aromatic solvent/product mixture to accelerate the dissolution of the latter, particularly in the case of vacuum residues. Heating from 60° C. to 100° C. is sufficient to dissolve the product in this case in a few minutes. In some cases (very stable products), a pre-dilution with n-heptane was carried out before the start of the measurements in order to limit the volume of paraffinic solvent (n-heptane) to be added to obtain flocculation.

Figure 6A:
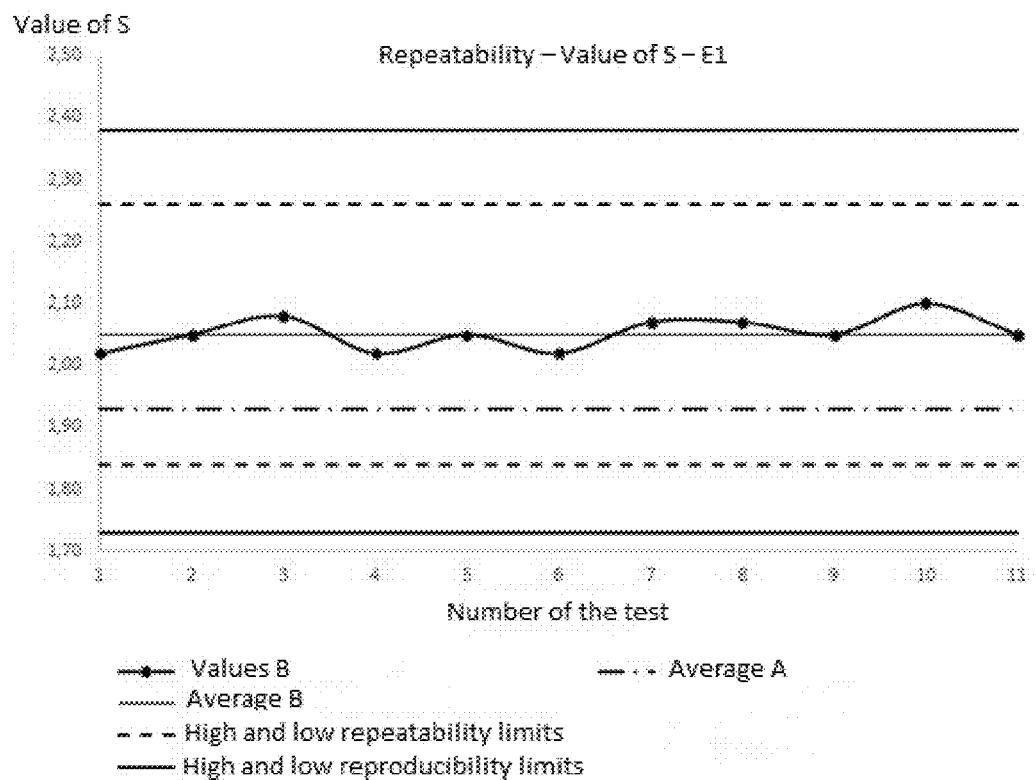
FIGS. 6a, 6b and 6c represents respectively the S, Sa and So values of the black product E1 as a function of the number of tests.
Figure 6B:
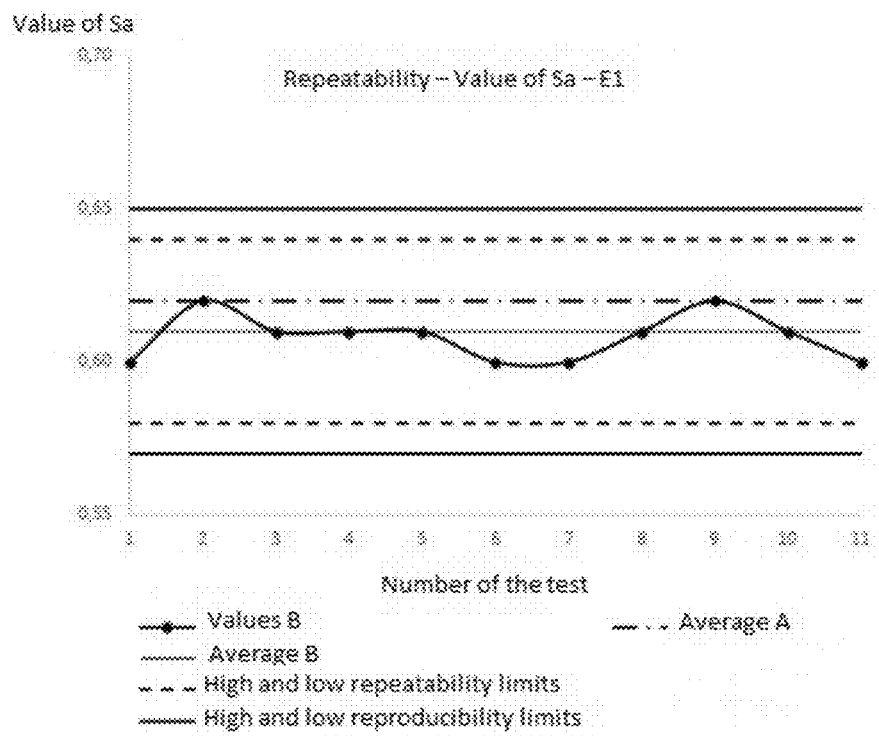
Figure 6C:
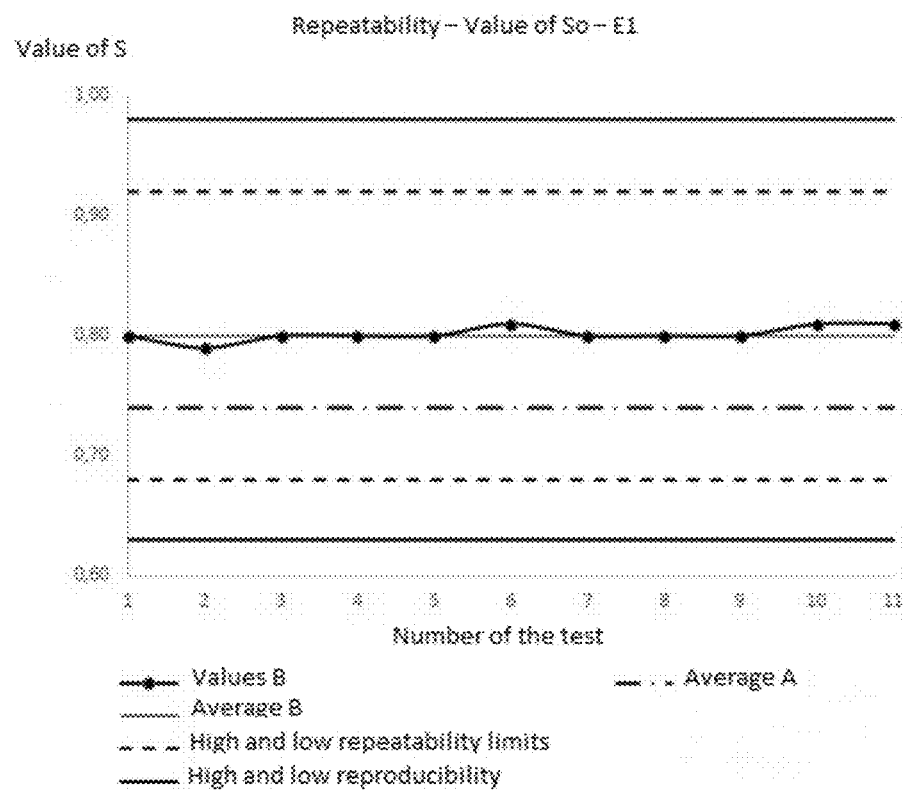
Figure 7:
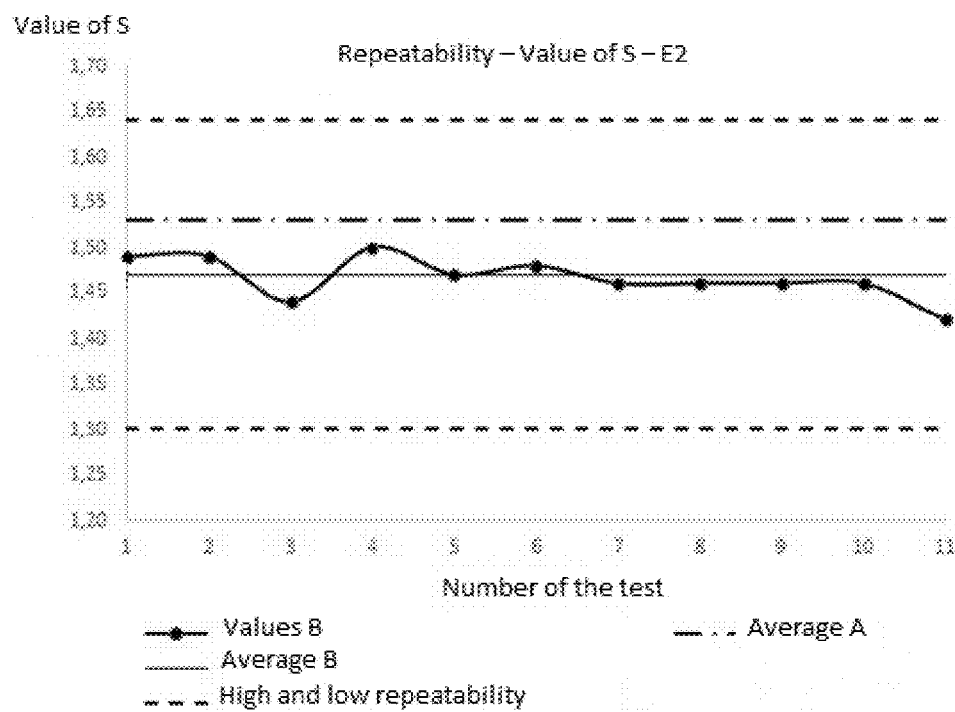
FIG. 7 represents the S values of the black product E2 as a function of the number of tests.

In this example, the black products tested correspond to:
E1: visbroken, non-fluxed atmospheric residue
E2: heavy fuel oil FIGS. 6a, 6b and 6c represent the S, Sa and So values of the black product E1 respectively, FIG. 7 represents the S value of the black product E2. The S, Sa and So values of the black product E2 measured with the method according to the invention are collated in Table 1.

TABLE 1

| Test | S | Sa | So |
| --- | --- | --- | --- |
| 1 | 1.49 | 0.43 | 0.85 |
| 2 | 1.49 | 0.43 | 0.85 |
| 3 | 1.44 | 0.41 | 0.85 |
| 4 | 1.50 | 0.43 | 0.86 |
| 5 | 1.47 | 0.43 | 0.84 |
| 6 | 1.48 | 0.43 | 0.85 |
| 7 | 1.46 | 0.40 | 0.87 |
| 8 | 1.46 | 0.41 | 0.86 |
| 9 | 1.46 | 0.41 | 0.87 |
| 10 | 1.46 | 0.41 | 0.86 |
| 11 | 1.42 | 0.40 | 0.86 |

Each figure brings together the average values calculated for 11 separate measurements for measurement method B according to the invention and for measurement method A. The repeatability and reproducibility values are calculated using the formulae in the ASTM D7157-18 standard (Revision 2018) from the average calculated for the measurements of each of the measurement methods A and B.

In each of these figures, are represented:
high and low limits of S, Sa and So taking repeatability into account (high and low repeatability limits), calculated by adding and subtracting the repeatability value calculated for measurement method B from the average of the measurements calculated for measurement method B respectively,
high and low limits S, Sa and So taking reproducibility into account (high and low reproducibility limits), calculated by adding and subtracting the reproducibility value calculated for measurement method B from the average of the measurements calculated for measurement method B respectively,
the average of the values obtained with the measurement method B according to the invention (Average B),
the values obtained with the measurement method B according to the invention (B values),
the average of the values obtained with measurement method A (Average A).

Curves 6a, 6b, 6c relating to sample E1 show that the S, Sa and So values obtained with measurement method B according to the invention are close to the values obtained with measurement method A, the SVA-130 probes® allowing implementation of the ASTM D7157-18 standard (Revision 2018) in compliance with the repeatability and reproducibility conditions defined in this standard. Similarly, curve 7 relating to sample E2 shows that the values of S obtained with measurement method B according to the invention are close to the values obtained with measurement method A, which a fortiori is also the case for Sa and So values.

In each FIG. 6a, 6b, 6c, 7 it can be seen that the minima and the maxima of the curves of the curves of the tests performed according to the measurement method B are between the low and high repeatability and reproducibility limits. In other words, the differences in values between various measurements obtained with the measurement method B according to the invention are low for both types of products.

Furthermore, the automation of the analysis allows the complete analysis to be carried out in less than one hour with the measurement method B according to the invention, whereas it takes more than two hours for method A in particular because of the operator time required to modify the optical path of the SVA-130® probes. In addition, the measurement method B according to the invention is also faster than using a device and method in accordance with document EP1751518 B1 due in particular to the automation of the dilution.

For each of the 11 measurements carried out with method B, the correlation coefficient $R^2$ of the precipitation curve (flocculation rate FR as a function of the inverse of the dilution) constructed with 3 points (P1, P2 and P3) varies:
from 0.9952 to 0.9999 for the product E1,
from 0.9936 to 0.9991 for the product E2.

The $R^2$ coefficient of the precipitation curve is thus greater than the minimum $R^2$ value (0.98) required by the standard.

Furthermore, the concept of efficiency expressed as the ASTM repeatability report (according to ASTM D7157-18-Revision 2018) to the repeatability calculated with the general formula (2×square root of 2×standard deviation, i.e. 2.83×standard deviation) was used to compare whether the repeatability of the ASTM D7157-18 standard (Revision 2018) is lower or greater than the device-specific repeatability according to the invention. In particular, the lower the repeatability, the more the values are repeatable and therefore less variable.

For the black product E1, this efficiency is 8.45, for the black product E2, it is 7.65.

It should be noted that the efficiency value of measurement method B is always greater than 1, which means that the repeatability of the device according to the invention is lower than the repeatability of the ASTM D7157-18 standard (Revision 2018.

The invention claimed is:
1. Device for measuring the flocculation threshold of a colloidal medium by adding an aliphatic solvent, comprising:
at least one measuring cell operating by direct optical transmission and having a measuring chamber intended to receive the medium, and, associated with each measuring cell:
a light emitter configured to emit a light beam entering the measuring chamber along an emission direction,
a photoelectric light receiver directly receiving the light beam exiting from the measuring chamber, the receiver being able to deliver a current when it receives a luminous flux,
a control system comprising:
a light emitter control system configured to vary the luminous intensity of the light beam emitted between a minimum and a maximum value,
a system for measuring the current delivered by the light receiver comprising:
a current-to-voltage converter receiving the current delivered by the light receiver and delivering a voltage, this converter comprising a controlled switch distributing the current in a circuit selected from at least two impedance circuits having different impedances,
a variable gain amplifier receiving the voltage supplied by the current-to-voltage converter and delivering a voltage equal to or proportional to the incoming voltage, an analogue-to-digital converter receiving the voltage output from the variable gain amplifier and delivering a digital signal representative of the amount of current supplied by the light receiver, a management system of the control system of each measuring cell, configured to control the light emitter control system, the switch of the current-to-voltage converter and the variable gain amplifier of each control system.

2. Measuring device according to claim 1, characterised in that the light emitter control system is a system for controlling the intensity of the current supplied to the emitter.

3. Measuring device according to claim 1, characterised in that the variable gain amplifyer is integrated in the analogue-to-digital converter.

4. Measuring device according to claim 1, characterised in that the impedance of each impedance circuit of the current-to-voltage converter is selected so that, in a range of current intensities, the voltage delivered by one of the impedance circuits has an amplitude range overlapping the amplitude range of the voltage delivered by another impedance circuit.

5. Measuring device according to claim 1, characterised in that each measuring chamber has two optical elements forming opposite walls of the measuring chamber, the minimum distance between the two optical elements in the emission direction having a value in the range of 0.4 to 1.2 mm, preferably 0.5 to 1 mm.

6. Measuring device according to claim 1, characterised in that the transmitter and the receiver of each measuring cell respectively have a light beam outlet opening and a sensitive area, and in that said outlet opening and said sensitive area each are positioned within a housing which is impervious to light rays coming from outside the measuring cell, each housing only leads to the measuring chamber, on opposite walls thereof.

7. Measuring device according to claim 1, characterised in that each measuring cell comprises a fluid inlet and outlet and in that the measuring device comprises a fluid circuit associated with each measuring chamber and connected to the fluid outlet thereof, the fluid circuit being equipped with a fluid flow member.

8. Measuring device according to claim 7, characterised in that each fluid circuit comprises one or more of the following:
    at least one tank and at least one liquid injection line connected to each tank,
    a mixing enclosure having an inlet and an outlet connected to the fluid circuit,
    at least one temperature control member.

9. Measuring device according to claim 7, characterised in that the fluid circuit forms a closed loop within which the medium circulates.

10. Measuring device according to claim 7, characterised in that it comprises means for continuously injecting liquid into the fluid circuit, in particular into the lines of the fluid circuit.

11. Method for measuring the flocculation threshold of a colloidal medium, in particular a colloidal medium containing asphaltenes, by adding an aliphatic solvent comprising the following steps:
    (i) the medium is introduced into a measuring chamber of a measuring cell operating by direct optical transmission, the measuring cell forming part of a device for measuring the flocculation threshold according to claim 1,
    (i1) optionally, a step of diluting said medium with a predetermined quantity of aliphatic solvent prior to step (i),
    (ii) using the management system of the device for measuring the flocculation threshold, a luminous intensity of the light beam emitted by the transmitter is set, the switch of the current-to-voltage converter is controlled to select an impedance circuit and a gain of the variable gain amplifier is selected so as to obtain a signal detectable by the analogue-to-digital converter,
    (iii) the flocculation threshold is determined using the measuring device after the addition of the amount of aliphatic solvent required for the flocculation, optionally the gain of the variable gain amplifier of the measuring device is modified during addition, optionally, the aliphatic solvent is added continuously, in particular at a constant flow, and the measurements are carried out using the measuring device while the aliphatic solvent is being added.

12. Method according to claim 11, wherein the emitter emits a light beam in the NIR range and the occurrence of flocculation is identified by determining the absorption peak.

13. Method according to claim 11, wherein the occurrence of flocculation is determined at a predetermined adjustable temperature.

14. Method according to claim 11, wherein the light consists of wavelengths belonging to a spectral range selected from among the near infrared spectral range and the infrared spectral range.

15. Method for determining the stability of a mixture comprising asphaltenes by implementing the process according to claim 11 at least twice on a medium containing the mixture and a given quantity of aromatic solvent, at different dilution rates, optionally, the aromatic solvent/aliphatic solvent pair used is the toluene/n-heptane pair.

* * * * *